(12) United States Patent
Goto et al.

(10) Patent No.: US 9,462,801 B2
(45) Date of Patent: Oct. 11, 2016

(54) METHOD FOR PRESERVING PANCREATIC ISLET, CONTAINER FOR PRESERVING PANCREATIC ISLET, AND KIT FOR TRANSPLANTING PANCREATIC ISLET

(75) Inventors: Masafumi Goto, Sendai (JP); Yoshihiro Yoshikawa, Osaka (JP); Kei Matsuo, Osaka (JP)

(73) Assignees: NIPRO CORPORATION, Osaka (JP); TOHOKU UNIVERSITY, Miyagi (JP)

( * ) Notice: Subject to any disclaimer, the term of this patent is extended or adjusted under 35 U.S.C. 154(b) by 1688 days.

(21) Appl. No.: 11/824,922

(22) Filed: Jul. 3, 2007

(65) Prior Publication Data
US 2008/0009061 A1 Jan. 10, 2008

(30) Foreign Application Priority Data

Jul. 5, 2006 (JP) .................................. 2006-186105

(51) Int. Cl.
| | | |
|---|---|---|
| C12M 1/00 | (2006.01) | |
| A01N 1/02 | (2006.01) | |
| C12M 1/04 | (2006.01) | |

(52) U.S. Cl.
CPC ............... *A01N 1/02* (2013.01); *A01N 1/0263* (2013.01); *A01N 1/0278* (2013.01); *C12M 23/14* (2013.01); *C12M 23/24* (2013.01)

(58) Field of Classification Search
CPC ..... A01N 1/02; A01N 1/0278; C12M 23/14; C12M 23/24
See application file for complete search history.

(56) References Cited

U.S. PATENT DOCUMENTS

| | | | | |
|---|---|---|---|---|
| 5,225,346 | A * | 7/1993 | Matsumiya et al. | 435/289.1 |
| 5,679,565 | A * | 10/1997 | Mullen et al. | 435/374 |
| 6,673,598 | B1 * | 1/2004 | Akers et al. | 435/298.2 |
| 2005/0032205 | A1 * | 2/2005 | Smith et al. | 435/297.5 |
| 2005/0153438 | A1 * | 7/2005 | Shirasu et al. | 435/293.1 |

FOREIGN PATENT DOCUMENTS

| | | |
|---|---|---|
| EP | 0471947 A1 | 2/1992 |
| JP | 05-229951 | 9/1993 |

OTHER PUBLICATIONS

Boyles, Salynn, "Live Donor Transplant May Treat Diabetes", Feb. 9, 2005, http: //diabetes.webmd.com/news/20050209/live-donor-transplant-may-treat-diabetes?print , pp. 1-3.*
Xu et al., "First results of hemocompatible membranes fabricated from acrylonitrile copolymers containing sugar moieties", Journal of Membrane Science, 2004, vol. 243, pp. 195-202.*
Bohak et al., "Novel Anchorage Matrices for Suspension Culture of Mammalian Cells", Biopolymers, 1987, vol. 26, pp. S205-S213.*
Goto et al., "Refinement of the Automated Method for Human Islet Isolation and Presentation of a Closed System for In Vitro Islet Culture," Transplantation, vol. 78, No. 9, Nov. 15, 2004, pp. 1367-1375.
Papas et al., "High-Density Culture of Human Islets on Top of Silicone Rubber Membranes," Transplantation Proceedings, vol. 37, No. 8, Oct. 1, 2005, pp. 3412-3414.
Shapiro et al., "Islet Transplantation in Seven Patients With Type I Diabetes Mellitus Using a Glucocorticoid-Free Immunosuppressive Regimen," The New England Journal of Medicine, vol. 343, No. 4, Jul. 27, 2000, pp. 230-238.
European Search Report issued in corresponding European Patent Application No. 07111875.6 dated Oct. 19, 2011 (9 pages).
Office Action issued in corresponding Japanese Patent Application No. 2006-186105 dated Jan. 30, 2012 with English translation (9 pages).
Transplantation Now, vol. 18, No. 4, Jul. 2005, pp. 394-400 (Concise Explanation can be found in English translation of Office Action—See 1).
Tanioka et al., "Excellence of the two-layer method (University of Wisconsin solution/perfluorochemical) in pancreas preservation before islet isolation," Surgery, vol. 122, Aug. 1997, pp. 435-442.

* cited by examiner

*Primary Examiner* — Laura Schuberg
(74) *Attorney, Agent, or Firm* — Kilyk & Bowersox, P.L.L.C.

(57) ABSTRACT

An object of the present invention is to provide a method for preserving pancreatic islet, a container for preserving pancreatic islet and a kit for transplanting pancreatic islet in order to effectively preserve the pancreatic islet. The present invention presents; a method for preserving a liquid including pancreatic islet in a container for preserving pancreatic islet, wherein at least a part of the container wall face consists of a film having an oxygen permeation coefficient of 2500 $cm^3/m^2 \cdot day \cdot atm$ or greater; a method for preserving a liquid including pancreatic islet in a container for preserving pancreatic islet, wherein at least a part of the container wall face consists of a film having a carbon dioxide permeation coefficient of 1000 to 20000 $cm^3/m^2 \cdot day \cdot atm$; and a container for preserving pancreatic islet for use in the above-described method, and a kit for transplanting pancreatic islet comprising the container for preserving pancreatic islet.

7 Claims, 1 Drawing Sheet

METHOD FOR PRESERVING PANCREATIC ISLET, CONTAINER FOR PRESERVING PANCREATIC ISLET, AND KIT FOR TRANSPLANTING PANCREATIC ISLET

BACKGROUND OF THE INVENTION

1. Field of the Invention

The present invention relates to a method for preserving pancreatic islet. In particular, it relates to a method for preserving pancreatic islet including a step of preserving a liquid containing pancreatic islet separated and purified from a living body in a container, wherein the container comprises a film having an oxygen permeation coefficient of 2500 $cm^3/m^2 \cdot day \cdot atm$ or greater. Furthermore, the present invention also covers a container for preserving pancreatic islet and a kit for transplanting pancreatic islet.

This application claims priority to JP patent application No. 2006-186105 filed Jul. 5, 2006.

2. Related Background of the Invention

Diabetes is disease caused by the disorder of action for controlling blood sugar in functions of the pancreas, and includes mainly two types, type I diabetes and type II diabetes. The type I diabetes appears at relatively early ages, and induces a symptom of strong invasion of insulin-producing cells due to autoimmune response, while the type II diabetes appears at middle and old ages, and is caused by difficulty in utilization of insulin. In Japan, it is estimated that 5% of diabetics are of type I diabetes and the number reaches about 300,000. These diabetics control blood sugar by insulin therapy, but can not be allowed to escape from the development of such complications as nephropathy, retinopathy, neuropathy. Furthermore, there are not few cases where blood sugar can not be controlled even by insulin therapy.

As a therapy method for fundamentally solving the above-described problems, there is pancreas transplantation. However, the pancreas transplantation includes such problems as heavy burden on a patient at transplant operation, and a high carcinogenic risk because a strong immune suppressor must be administered even after the transplantation.

As a novel transplantation therapy that can replace such pancreas transplantation, in recent years, pancreatic islet (also called Langerhans islet) transplantation technique has been energetically studied. The pancreatic islet means the group of endocrine cells that are scattered in an island shape in the tissue of the pancreas and contain β-cells secreting insulin. In addition, the pancreatic islet transplantation means a transplantation therapy in which pancreatic islet is separated from the pancreas offered from a donor to prepare a dispersion liquid of the pancreatic islet, and then the dispersion liquid is percutaneously administered to a patient, and a revolutionarily novel protocol was established by University of Alberta, Edmonton, Canada (Edmonton Protocol: CURRENT HUMAN ISLET ISOLATION PROTOCOL, (Edition: JONATHAN et al., Publication: Medical Review Co., Ltd)) in 2000.

In actual conditions of the pancreatic islet transplantation in Japan, pancreatic islet was successfully transplanted from a cardiac arrest donor for the first time in Japan, in Department of Transplantation, Kyoto University, in April 2004. In the future, more clinical cases must be accumulated. Also, business organizations that participate in the health industry must cooperate with this. There are few patent applications in Japan regarding the pancreatic islet transplantation, but, for example, JP-A-05-229951 discloses an invention that uses a gelatin solution as a specific gravity liquid.

The pancreatic islet transplantation has following merits.

Since it is percutaneously administered, burden on a patient at transplant operation is light (no abdominal operation and full anesthesia are required).

Even when immunological rejection occurs, there is no need for removing graft because β-cells disappear.

A small dose of immunosuppressive agent is all that is needed in a patient after the transplantation.

Even pancreas from donors that is not applicable for pancreas transplantation such as that from donors who died from cardiac arrest or arterial sclerosis can be used.

However, about 10 to 18 hours are required from pancreatectomy from a donor to preparation of pancreatic islet for the transplantation. Thus the prepared pancreatic islet must be preserved appropriately so that the pancreatic islet does not lose the vital force. In conventional methods, the preservation has been carried out by using such polystyrene tools as a flask or petri dish for culture.

However, since many of β-cells constituting pancreatic islet are deactivated or deadened in around 24 hours after the separation and purification of pancreatic islet, it is found that there is temporal restriction from the preparation of the pancreatic islet to the completion of transplant operation. For example, there is such a case that the transplant operation can not be carried out because the patient feels not well even when the preparation of the pancreatic islet transplantation has been completed, and that β-cells may be deactivated or deadened. Polystyrene petri dishes and flasks for culture conventionally used for a preservation container have a low oxygen permeability. A large amount of air was therefore required in the container, and only a small amount of pancreatic islet suspension prepared by suspending pancreatic islet could be put in the container. For example, a 100 mm petri dish can preserve only around 5 ml of a pancreatic islet suspension. Consequently, for preserving pancreatic islet separated from one pancreas, around 100 petri dishes has had to be used with a great deal of effort. In addition, when a petri dish or flask is used, pancreatic islet may adhere to the wall surface of the container, resulting in the loss of the pancreatic islet. Furthermore, containers made of polystyrene have a lid or a screw-type removable cap and have no sealing performance, so that the pancreatic islet may be contaminated with bacteria or viruses. If β-cells are deactivated, deadened, lost, contaminated and/or influenced caused by these problems, the will of the donor can not be respected.

Furthermore, at pancreatic islet transplantation, pancreatic islet has been collected from each of petri dishes or flasks as required, and has been temporarily preserved in a bag made of vinyl chloride and carried to an operation room. Concretely, a pancreatic islet liquid is aspirated from a petri dish or flask with a commercially available pipette or syringe, and then a port of the bag is punctured with a plastic needle or the like provided with a rubber coinjection part, through which the pancreatic islet is inpoured by a syringe with a needle. However, when preserved number is large, the collection and injection into a bag have had to be repeated many times, which takes a long time and so carries risks of bacterial contamination.

SUMMARY OF THE INVENTION

An object of the present invention is to provide a method and a container for effectively preserving pancreatic islet, and a kit capable of safely carrying out transplantation of pancreatic islet.

As a result of intensive studies on preserving pancreatic islet even after the separation and purification thereof in circumstances for effectively maintaining the activity of β-cells, the present inventors came to perfect the present invention by discovering that it is possible to effectively preserve pancreatic islet when pancreatic islet is preserved using a container for preserving pancreatic islet having an appropriate oxygen permeation coefficient.

That is, the present invention includes the following items.

1. A method for preserving pancreatic islet, including a step of preserving a liquid containing pancreatic islet separated and purified from a living body in a container, wherein at least a part of the wall face of the container consists of a film having an oxygen permeation coefficient of 2500 $cm^3/m^2 \cdot day \cdot atm$ or greater.

2. The method for preserving pancreatic islet according to previous item 1, wherein at least a part of the wall face of the container consists of a film having a carbon dioxide permeation coefficient of 1000-20000 $cm^3/m^2 \cdot day \cdot atm$.

3. The method for preserving pancreatic islet according to previous item 1 or 2, wherein the film is at least one selected from a group consisting of low density polyethylene, medium density polyethylene, polymer blend of low density polyethylene and medium density polyethylene, polyvinyl chloride, poly(ethylene-vinyl acetate) copolymer, poly(ethylene-ethyl acrylate) copolymer and poly(ethylene-methacrylate) copolymer.

4. The method for preserving pancreatic islet according to any one of previous items 1 to 3, wherein the film has a pure water contact angle of 85 degrees or greater.

5. The method for preserving pancreatic islet according to any one of previous items 1 to 4, wherein the container further includes a filter for exchanging a preservative liquid.

6. The method for preserving pancreatic islet according to any one of previous items 1 to 5, wherein the container has a bag-like figure produced of two of the films, is further provided with a port for injecting and ejecting the liquid, and has a sealed edge portion tapered toward the port.

7. The method for preserving pancreatic islet according to any one of previous items 1 to 6, wherein the container has a bag-like figure produced of two of the films, and the volume of the liquid containing pancreatic islet to be preserved in the container is such a volume that the maximum value of the container thickness, the distance between the two films, is within the range of 3 to 10 mm, when the liquid containing pancreatic islet is stored in the container and the container is placed on a horizontal plane so that the film surface of the container contacts the plane.

8. A container for preserving pancreatic islet including the container for use in the method for preserving pancreatic islet according to any one of items 1 to 7.

9. A kit for transplanting pancreatic islet, including:
the container for preserving pancreatic islet according to item 8;
a first container for preparing a solution for pancreatic islet transplantation and administering the solution for pancreatic islet transplantation;
a second container previously containing a solvent for the solution for pancreatic islet transplantation; and
a communicating means for communicating the first container and the second container, which is provided with a closing means capable of repetitive communication.

10. The kit for transplanting pancreatic islet according to previous item 9, wherein at least a part of the wall face of the first container consists of a film having an oxygen permeation coefficient of 2500 $cm^3/m^2 \cdot day \cdot atm$ or greater.

11. The kit for transplanting pancreatic islet according to previous item 9, wherein at least a part of the wall face of the second container consists of a film having an oxygen permeation coefficient of 10 $cm^3/m^2 \cdot day \cdot atm$ or smaller, and a water vapor permeability of 10 $g/m^2 \cdot day \cdot atm$ or smaller.

12. The kit for transplanting pancreatic islet according to previous item 11, wherein the film includes at least one film selected from a group consisting of stretched nylon, polyester, polyvinylidene chloride, polyvinylidene chloride-coated stretched nylon, polyvinylidene chloride-coated polyester, polyvinyl chloride-coated polypropylene, polyvinyl alcohol, poly(ethylene-vinyl alcohol) copolymer, aluminum-evaporated polyester and silica-coated polyester.

According to the method and the container of the present invention, it is possible to preserve pancreatic islet over a long period of time. Sufficient time can be therefore given from the preparation of pancreatic islet to transplant operation, and thereby a burden on an operator is reduced. In addition, the operator can perform transplant operation when a patient is on top conditions. Furthermore, risks of deactivation, death and loss of β-cells caused by unsuitable preserving conditions are remarkably reduced, and a will of a donor is therefore respected.

EXPLANATION OF NUMERALS

1: Container
2: First Container
3: Second Container
11: Film
12: Port
13: Taper

DESCRIPTION OF THE PREFERRED EMBODIMENTS

Figure 1:
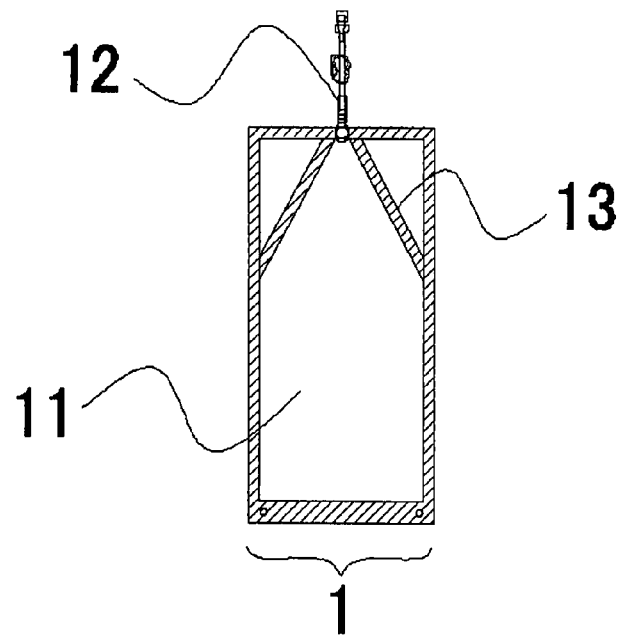
FIG. 1 shows a container 1 for preserving pancreatic islet of the present invention.

Hereinafter, the present invention will be described in detail with reference to the drawings, but the present invention is not limited to the following description. The container for preserving pancreatic islet of the present invention means a container for storing and preserving pancreatic islet separated and purified from the pancreas. The container may have either a housing shape or a bag shape (which means a bag-like form). Nevertheless, from the viewpoint of easiness of production and compactness in disposal, a bag shape is preferred. Furthermore, the container may be provided with appropriate parts as required. For example, when a container 1 has a housing shape, it may be provided with a screw lid screwing together with the mouth portion of the housing. For example, when the container 1 has a bag shape as shown in FIG. 1, it may be provided with a port 12 for injecting and ejecting a liquid to be stored. On this occasion, a construction including an edge portion of two films heat-sealed by a heat-sealing method (sealed edge portion) may form a taper 13 toward the port 12.

As for the size of the container 1, one side is preferably around 150-250 mm, and the other one side is preferably around 300-400 mm, from the viewpoint of easiness of handling and the size of an incubator. As for the volume of the liquid to be charged in the container 1 of a bag shape, the volume in such a case that the thickness of the container 1 being the distance between two films is 3-10 mm, preferably 4-8 mm when the container 1 is left at rest in a horizontal state so that oxygen is sufficiently diffused in the liquid and the pancreatic islet does not adhere to the wall surface of the container, is preferable. Because, when the thickness is smaller than 3 mm, the pancreatic islet may adhere to the wall surface of the container, and when it is greater than 10 mm, oxygen may be hardly diffused in the liquid. The volume of the liquid in this case is not particularly limited, but it is preferably about 200-600 ml, more preferably about 300-500 ml. Furthermore, the volume of the liquid is around 5-40% of the volume of the container 1, preferably around 7.5-30%, but the present invention is not limited to these.

The container 1 for preserving pancreatic islet of the present invention is characterized in that at least a part of the wall face of the container consists of a film having an oxygen permeation coefficient of 2500 $cm^3/m^2 \cdot day \cdot atm$ or greater. The wall face of the container means the surface to which the liquid to be stored in the container 1 contacts. In addition, at least a part of the wall face of the container 1 means that the entire film does not necessarily have the oxygen permeation coefficient, but the entire film may have the oxygen permeation coefficient. Specifically, to 100% of the total area of the wall face of the container 1, 5% or more, preferably 50% or more, especially preferably 80% or more of area has the oxygen permeation coefficient, nevertheless the case of 100% where the whole film has the oxygen permeation coefficient is most preferable from the viewpoint of the easiness in producing the container.

If the oxygen permeation coefficient is 2500 $cm^3/m^2 \cdot day \cdot atm$ or greater, the upper limit is not especially limited, but it is 2500-4000 $cm^3/m^2 \cdot day \cdot atm$, preferably 3000-3500 $cm^3/m^2 \cdot day \cdot atm$. The oxygen permeation coefficient can be measured by JIS K7126-1987 differential pressure method. In the case that the oxygen permeation coefficient of the film is smaller than 2500 $cm^3/m^2 \cdot day \cdot atm$, the result of preservation of the pancreatic islet is not satisfactory, and when it takes a long time from the separation and purification of the pancreatic islet to pancreatic islet transplantation, the β-cells may be deactivated.

In the case that a liquid for preserving pancreatic islet to be stored in the container 1 has buffering ability based on sodium hydrogen carbonate, from the viewpoint of maintenance of the pH of the preservative liquid, in the container for preserving pancreatic islet of the invention, at least a part of the wall face of the container 1 is preferably made of a film having a carbon dioxide permeation coefficient of 1000-20000 $cm^3/m^2 \cdot day \cdot atm$. The carbon dioxide permeation coefficient may be 1000-20000 $cm^3/m^2 \cdot day \cdot atm$, preferably 3000-11500 $cm^3/m^2 \cdot day \cdot atm$, and more preferably 5000-10000 $cm^3/m^2 \cdot day \cdot atm$.

Examples of materials that meet the oxygen permeation coefficient include low density polyethylene, medium density polyethylene, polymer blend of low density polyethylene and medium density polyethylene, polyvinyl chloride, poly(ethylene-vinyl acetate) copolymer, poly(ethylene-ethyl acrylate) copolymer and poly(ethylene-methacrylate) copolymer. Among these, such materials including at least low density polyethylene as low density polyethylene, and polymer blend of low density polyethylene and medium density polyethylene are preferred. These materials can bear with gamma sterilization, and has a high transparency to allow observation of internal situations.

A production of the container body including a film having an oxygen permeation coefficient of 2500 $cm^3/m^2 \cdot day \cdot atm$ or greater as described above can be arbitrarily prescribed by a person skilled in the art in consideration of physical properties of the material to be used or the like, and so is not especially limited. For example, in the case that the container is formed in a bag shape, however, from the viewpoint of the cost and easiness of the production, it can be produced by a heat seal method. For the width of the heat-sealed part, the range where the content does not leak is sufficient, that is, it may be about 2-20 mm, preferably about 5-10 mm.

Furthermore, it is preferred to prevent the loss of pancreatic islet due to the adhesion of preserved pancreatic islet to the wall face of the container. For preventing the adhesion of the pancreatic islet to the wall face of the container 1, the pure water contact angle of the film forming the container 1 may be about 85 degrees or larger, specifically about 85-100 degrees, preferably about 90-100 degrees. In the case that the pure water contact angle is smaller than 85 degrees, the pancreatic islet may adhere to the film. Measurement of the contact angle can be conducted, for example, with a contact angle meter, an optical microscope and the like, but is not limited to these. Such preferable materials include those that contain at least low density polyethylene such as low density polyethylene, and polymer blend of low density polyethylene and medium density polyethylene as described above.

Additionally the container 1 for preserving pancreatic islet of the present invention is preferably further provided with a filter for exchanging a preservative solution. The filter for exchanging a preservative solution means such a filter that does not allow pancreatic islet to pass through but that allows a liquid for dispersing the pancreatic islet (preservative solution) to pass through and thereby facilitates exchange of the preservative solution in the container. For the material of the filter, porous one may be used, including, for example, woven fabric, nonwoven fabric and the like. Examples of the component thereof include polyester-based resins such as polyethylene terephthalate and polyolefin-based resins such as polyethylene and polypropylene. Furthermore, the volume of the filter case is about 1-40 ml, preferably about 1-20 ml, particularly preferably about 1-10 ml in consideration of the flow volume of the preservative solution, but is not limited to this. Regarding the diameter of fiber used for the woven fabric and nonwoven fabric and the filling rate of the filter relative to the volume of the case, in consideration of separation of the pancreatic islet from the preservative solution, the passage diameter of the filter is about 1-40 μm, preferably about 5-30 μm, and the filling rate to 100% of the case volume is about 50-99%, preferably about 70-90%, but are not limited to these.

The obtained pancreatic islet can be preserved by being directly stored in the container 1 of the present invention, for example, by being injected with a syringe in the case that the container 1 of the present invention is provided with a syringe-connecting port.

As for the volume of the dispersion liquid to be injected into the container 1, it is preferable that oxygen is sufficiently diffused so that the β-cells of the pancreatic islet in the container are made harder to deactivate. For the activity of β-cells, a survival rate is an indicator, and it is suitable that the rate is at least 25%, preferably at least 30%. By using the conservation of the activity of β-cells as a marker, preservation conditions can be determined.

Based on this viewpoint, for example, it is preferred that, in the case where the container 1 made of two films having a size of 200×350 mm contains a liquid of 200-400 ml and is placed on a horizontal plane so that the film surface of the container 1 abut on the plane, the maximum thickness of the container 1 that is the distance between the two films is set to 3-10 mm. As for a preservation condition, it is preferably under an atmosphere of 5% carbon dioxide and at 37° C. The period of preservation is about 1-4 days. Since it has been better that the pancreatic islet is maintained for one day in the conventional preservation method, it is said that the invention exerts an especial advantage. Thereby, the time restriction from the preparation of the pancreatic islet to the administration to a patient can be eliminated.

Respective steps of Edmonton Protocol (the offer of pancreas from a donor: 1, and the separation and purification of pancreatic islet from the pancreas: 2) (see CURRENT HUMAN ISLET ISOLATION PROTOCOL, (Edition: JONATHAN et al., Publication: Medical Review Co., Ltd)) are as follows. These steps are such items that a person skilled in the art having learned the Protocol can practice as required, and the present invention is not limited to these.

1. Offer of Pancreas from Donors

Donors mainly include cardiac arrest donors, brain death donors and living body donors. The cardiac arrest donor means a human being who is decided to be in a state of cardiac arrest, that is, the person, before decision of cardiac arrest, or a family member of the person, after the decision of cardiac arrest, indicates a willingness to donate the organ. The brain death donor means a human being who is decided to be in a state of brain death, that is, the person, before decision of brain death, or a family member of the person, after the decision of brain death, indicates a willingness to donate the organ. The living body donor means a healthy donor who indicates a willingness to donate the organ.

Medical adaptability of a donor is performed on the basis of the standard of "Tissue Transplantation" by The Japan Society for Transplantation, Working Group 6; and "Guideline on Medical Practice Using Human Tissues" by Japanese Society of Tissue Transplantation. For example, in the case where the donor is a cardiac arrest donor, it is as given below.

The age is, as a rule, 70 years or younger.

The allowed time from the arrest to the start of the perfusion of the pancreas (warm blood obstruction time) is, as a rule, 30 minutes or less.

The check of such exceptive items as infectious diseases is carried out according to the guideline of the Society of Tissue Transplantation.

The isolation of the pancreas from a donor varies depending on the type of donors. For example, in the case where the donor is a cardiac arrest donor or a brain death donor, about 50-100% of the pancreas of the donor is excised to isolate. For example, in the case where the donor is a living body donor, about 50-70% of the pancreas of the donor is excised to isolate.

The pancreas having been excised from a donor is once preserved. It is preserved by a dip preservation method using such a commercially available organ preservative solution as a Eurocollins solution or a UW solution, and preferably by a two-layer method. The two-layer method is a publicly known procedure in the field of preserving organs, in particular the pancreas, and is the method that is also recommended in the standard of "Tissue Transplantation" by The Japan Society for Transplantation, Working Group 6; and "Guideline on Medical Practice Using Human Tissues" by Japanese Society of Tissue Transplantation. Specifically, in a liquid of two layers including a lower layer of perfluorocarbons (PFCs) and an upper layer of an organ preservative solution (mainly a UW solution), an organ is placed in the lower layer of perfluorocarbons, an instrument through which the pancreas can not pass but the liquid and gas dispersed in the liquid can pass is arranged at the interface of two layers, and then oxygen is bubbled in the lower layer of perfluorocarbons to preserve the organ.

2. Separation and Purification of Pancreatic Islet from Pancreas

Next, pancreatic islet is separated and purified from the excised pancreas. The separation and purification mainly comprises the following three steps.

(1) A step for swelling the pancreas with an enzyme (swelling step)

(2) A step for degrading the pancreas with an enzyme (degradation step)

(3) A step for separating pancreatic islet from other tissues by a density gradient centrifugation method (separation step)

(1) Step for Swelling the Pancreas with an Enzyme (Swelling Step)

The step is a step for permeating an enzyme evenly into the pancreas for the purpose of effectively degrading the pancreas in the subsequent step. The enzyme for use in the step is formed by blending collagenase I and collagenase II with a neutral protease having a high specific activity. It can be purchased from Roche Diagnostics (product name: Liberase series). The use amount of the enzyme may be one vial (about 0.5 g) per one excised pancreas, although it depends on the size of the excised pancreas. In the method that the enzyme is permeated into the entire pancreas, at least a wire net and a tray under the wire net are firstly placed in a clean bench. Next, the pancreas is placed on the wire net. On this occasion, in the case where spleen and/or duodenum also exists with the pancreas, they are previously excised. Then, the enzyme is introduced via such vessel as a vein in the pancreas with a catheter or a cannula. After a period of time, the enzyme permeates the pancreas from the vessel wall and, finally, oozes from the pancreas to the outside. The enzyme that has oozed from the pancreas accumulates in the tray, which is drawn manually or pumped, and sprinkled on the pancreas again. By repeating these operations for about 15-30 minutes, the pancreas is swelled with the enzyme. Here, since the enzymatic reaction must not proceed during this step, the operation is carried out using the chilled enzyme. The chilling temperature is specifically about 0-8° C., preferably about 2-6° C.

(2) Step for Degrading the Pancreas with an Enzyme (Degradation Step)

Next, the swollen pancreas is degraded through an enzymatic reaction and mechanically. Specifically, the swollen pancreas and about 4-8 iron balls of a marble size are put in a stainless container. The pancreas to be put in the stainless container is preferably cut into an appropriate size with a surgical knife, surgical scissors or the like. Although the number of pieces of the cut pancreas can not be uniquely determined because of its dependence on the size of the pancreas, it is around 3-8 pieces. The iron ball preferably has the outer diameter of about 5-10 mm, and the weight of about 10-50 g. The stainless container is provided with a liquid inlet port and a liquid outlet port, and the liquid inlet port and the liquid outlet port are connected with each other through a conduit tube. The conduit tube forms a circulative circuit, through which an enzyme liquid is sent and circulated with a pump. The liquid to be circulated is preferably the Hanks' buffer salt solution (HBSS). By circulating the HBSS prior to the start of the degradation step, the priming is carried out. By putting the swollen pancreas in the stainless container after the end of the priming, the enzyme contained in the pancreas is diluted with the HBSS. It is better that the solution sending velocity is around 120-180 ml/min. The circuit is provided with a temperature-controlling means which maintains the activation temperature of the enzyme solution to initiate the enzyme reaction. In the case of the enzyme (trade name: Liberase), the temperature is about 37-42° C. At the same time, the stainless container is vibrated up and down in a sealed state. The vibration operation may be carried out either with a device or manually. In the case where a device is used, the vibration has preferably an amplitude of around 50-300 mm, and a cycle of around 30-90 times/sec. The operation of this step is carried out for about 15-40 minutes. As a result, the iron balls of the marble size put in the stainless container degrade mechanically the pancreas. Through the enzyme reaction and mechanical degradation, the pancreas becomes a liquid material including the pancreatic islet. During the operation, sampling is carried out arbitrarily to check that the pancreas has been sufficiently degraded with a microscope. Then cells are collected together with the enzyme liquid from a collecting port and chilled at 4-8° C. to stop the enzyme reaction. A container for the collection is not particularly limited, but the use of a 250 ml centrifugal tube is convenient because centrifugation can be directly carried out to separate the cells from the enzyme liquid. About 5 L of the solution is collected, which is centrifuged and concentrated to about 200 ml.

(3) Step for Separating the Pancreatic Islet from Other Tissues By Density Gradient Centrifugation Method (Separation Step)

Then, pancreatic islet is separated from the liquid material containing the pancreatic islet. For the separation, a density gradient centrifugation method is used. The operation thereof is within such a range that a person skilled in the art can do, and a commercially available density gradient centrifugal apparatus may be used. From the viewpoint of an easy operation, however, the use of an apparatus using a bag is preferred. Such apparatus can be purchased, for example, from COBE Inc. (trade name: COBE2991). For a specific gravity liquid for use in the centrifugation, the use of a commercially available Ficoll-Conray liquid, Ficoll-Hypaque liquid or Bicoll liquid is sufficient. The density gradient centrifugation method is difficult to unconditionally mention because fractionation of the eluate to obtain the pancreatic islet from the start of the centrifugation depends on the rotation number of the centrifugal separation and the type of the specific gravity liquid, but the practice on unified conditions according to the Edmonton Protocol leads to stable fractionation. For example, when a centrifugal circuit is charged with a liquid having a specific density of 1.077, into which a liquid having a specific density of 1.100 is gradually flowed while being subjected to centrifugation, a density gradient from 1.077 to 1.100 occurs in the centrifugal circuit. After that, the liquid material obtained in the degradation step is flowed into the circuit to separate and collect the pancreatic islet. On this occasion, the pancreatic islet (β-cell) is separated into the fraction of specific density 1.077, and other exocrine tissues are separated into the fraction of specific density 1.100. The pancreatic islet is collected by selecting the fraction of the eluate containing the pancreatic islet while arbitrarily observing the eluted liquid from the beginning of the centrifugation. Specifically, the eluted liquid is sequentially fractionated from the collection port in increments of about 20 ml, while the eluate is arbitrarily observed. Here, the use of a polystyrene T-type 25 cm² flask as a container for the fractionation is preferred because it is possible to observe cells contained in the fractionated liquid with a microscope. From the centrifugal separator, firstly cells of exocrine tissues are eluted. In the case where the step is carried out according to the Edmonton Protocol, the largest amount of the pancreatic islet is observed in the fraction that is obtained after the liquid of about 200 ml has been eluted, therefore the eluate after that is collected. The volume of the liquid to be collected is about 20-120 ml. The collected eluate is gathered in a 250 ml centrifugal tube, which is then centrifuged at 224 g to remove the specific gravity liquid. Then, the pancreatic islet is suspended again in a preservative solution. For the preservative solution, for example, a CMRL medium is mainly used. To the medium, such supplements as antibiotics, antifungals may be arbitrarily added, but they are not limited to these.

3. Preservation of Pancreatic Islet

The pancreatic islet thus obtained according to the above steps may be directly stored in the container 1 of the present invention, and, for example, in the case where the container 1 of the present invention is provided with a port for connecting a syringe, it may be injected with a syringe. The amount of the dispersion liquid to be injected into the container 1 is preferably so determined that oxygen sufficiently diffuses over the dispersion liquid in order to make it harder for the β-cell activity of the pancreatic islet in the container to be deactivated. The activity of β-cells is represented by the surviving rate as an indicator and, suitably, is at least 25%, preferably at least 30%. The preservation conditions can be thus determined by using the maintenance of the β-cell activity as a marker. From this viewpoint, for example, it is preferred that, when the container 1 made of two films having a size of 200×350 mm stores a liquid of 200-400 ml and placed on a horizontal plane that the film surface of the container 1 abuts on the plane, the maximum thickness of the container 1 that is the distance between two films is 3-10 mm. As for a preservation condition, it is preferably under an atmosphere of 5% carbon dioxide and at 37° C. The period of preservation is about 1-4 days. Since it has been better that the pancreatic islet is maintained for one day in the conventional preservation method, it is said that the invention exerts an especial advantage. Thereby, the time restriction from the preparation of the pancreatic islet to the administration to a patient can be eliminated.

The kit for transplanting pancreatic islet means a kit formed by the container 1 for pancreatic islet transplantation of the present invention; a first container 2 in which at least a part of the wall face of the container consists of a film having an oxygen permeation coefficient of 2500 cm³/m²·day·atm or greater; and a second container 3 in which at least a part of the wall face of the container includes a gas barrier film having an oxygen permeation coefficient of 10 cm³/m²·day·atm or smaller and a moisture permeability (water vapor permeability) of 10 g/m²·day·atm or smaller, wherein container 2 and container 3 are communicated by a connecting tube having a communicable means.

Figure 2:
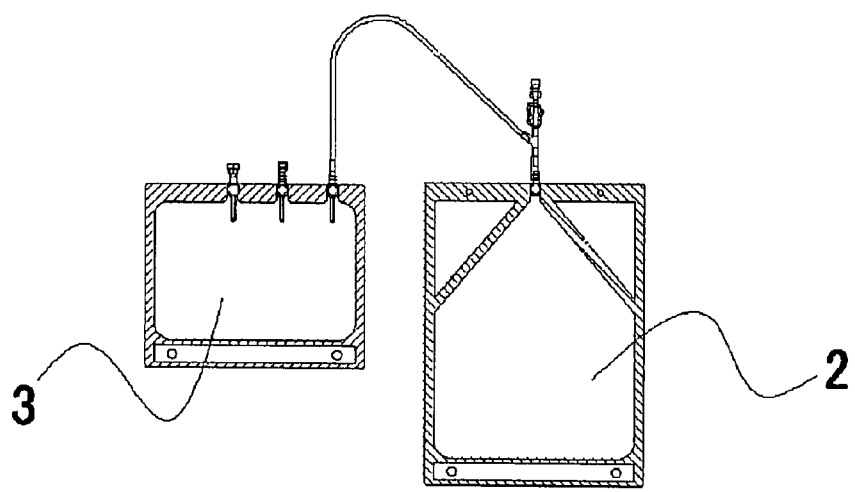
FIG. 2 shows a configuration that a first container 2 and a second container 3 communicate with each other in a pancreatic islet preservation kit of the present invention.

FIG. 2 shows the state that the first container 2 and the second container 3 are communicated with each other.

The film for the first containers 2 comprises any one of, for example, low density polyethylene, medium density polyethylene, polymer blend of low density polyethylene and medium density polyethylene, polyvinyl chloride, poly(ethylene-vinyl acetate) copolymer, poly(ethylene-ethyl acrylate) copolymer and poly(ethylene-methacrylate) copolymer and the like.

The film of the second container 3 comprises at least one of a group consisting of, for example, stretched nylon, polyester, polyvinylidene chloride, polyvinylidene chloride-coated stretched nylon, polyvinylidene chloride-coated polyester, polyvinyl chloride-coated polypropylene, polyvinyl alcohol, poly(ethylene-vinyl alcohol) copolymer, aluminum-evaporated polyester, silica-coated polyester.

Prior to transplantation, the pancreatic islet is once taken out of the preservation container and put in a container for centrifugation, which is then subjected to centrifugation to separate the pancreatic islet from the preservative solution. The separated pancreatic islet is charged in the first container 2. On this occasion, in the case where the first container 2 is provided with a port for connecting a syringe, the pancreatic islet can be moved easily to the first container 2. In the second container 3, chemicals to be used by being blended with the pancreatic islet at the transplantation are charged. The chemical means a normal saline solution etc., with which a supplement may be mixed in order to increase the graft survival of the pancreatic islet. The transplantation liquid having been charged in the second container 3 is transported to the first container 2 just before the transplantation. On this occasion, the first container 2 and the second container 3 are connected with each other by a connecting tube having a communicable closing means. The closing means is one embodiment that achieves a sealed state and block off the passage of the medium in the communicating means. The means for closing the communication can easily open the communication again, and includes the closing by such a nipping body as a clip, the closing by a communicating piece (foldable stick), or the closing by a weak sealing and the like. In addition, that communication can be opened again is one embodiment of capability of unsealing. In an operation room, chemicals in the second container 3 are transported in the first container 2 and sufficiently blended. Then, the first container 2 is connected with a catheter, and the pancreatic islet can be percutaneously injected to the hepatic portal vein under the echo.

EXAMPLES

Hereinafter, the present invention is described by presenting examples, but the invention is not limited to these.

Example 1

Production of the Preservation Container of Pancreatic Islet of the Present Invention A polyethylene film was cut into 170×350 mm-sized pieces. Two of these were put together and the edges of 5 mm thereof were heat-sealed by a heat seal method to form a container for preserving pancreatic islet 1 suitable for the preservation volume of 400 ml (FIG. 1). The oxygen permeation coefficient of the polyethylene film is 3000 $cm^3/m^2 \cdot day \cdot atm$.

Comparative Example 1

A Preservation Container of Pancreatic Islet as a Control

As a control for the present Example, a container having an oxygen permeation coefficient of 2000 $cm^3/m^2 \cdot day \cdot atm$ (by Baxter Inc.) was used.

Reference Example 1

Separation of Pancreatic Islet from the Pancreas

The pancreas of a pig was provided from Sendai Central Meat Wholesale Markets. The pancreas was preserved by the two-layer method, and preparation for the following steps was carried out.

(1) Step for Swelling Pancreas with Enzyme (Swelling Step)

Firstly, At least a wire net and a tray under the wire net were placed in a clean bench. Next, the pancreas was placed on the wire net, into which an enzyme was introduced from a vein of the pancreas by using a catheter. As for the enzyme, an enzyme formed by blending collagenase I and collagenase II with neutral protease having a high specific activity (by Roche Diagnostics K.K., product name: Liberase). After a period of time, the enzyme oozed from the pancreas to the outside, which was drawn up manually and sprinkled to the pancreas again. By repeating these operations for about 25 minutes, the pancreas was swelled with the enzyme. In this step, in order not to allow the enzyme reaction to proceed, the enzyme was chilled at about 4° C.

(2) Step for Degrading Pancreas with Enzyme (Degradation Step)

A circulative circuit for carrying out the enzyme reaction and mechanical degradation provided with a stainless container and a temperature-controlling means was subjected to priming with the Hanks' buffer salt solution (HBSS). In the stainless container, the pancreas segments having been cut into pieces by a surgical knife and six iron balls having a marble size (outer diameter: about 10 mm, weight: about 20 g) were put. The temperature of the temperature-controlling means is set to about 40° C., and the HBSS was circulated at a liquid feed velocity of about 150 ml/min to initiate the enzyme reaction. At the same time, by placing a stainless container housing to a vibratory apparatus to initiate mechanical degradation with the amplitude of about 200 mm and a cycle of about 60 times/sec. In 60 minutes, the iron balls in the stainless container were removed and the liquid material was collected.

(3) Step for Separating Pancreatic Islet from Other Tissues by Density Gradient Centrifugation Method (Separation Step)

The liquid material obtained in the above (2) was treated by a density gradient centrifugation method to separate pancreatic islet from the liquid material. For the density gradient centrifugation apparatus, one that had been purchased from COBE Inc. (trade name: COBE2991) was used. For the specific gravity liquid for use in the centrifugation, a Bicoll liquid was selected. The centrifugation was carried out under the condition of rotation number of about 2300 rpm. Firstly, a liquid having a specific density of 1.077 was charged in the centrifugal circuit, into which a liquid having a specific density of 1.100 was gradually flowed while being subjected to centrifugation, resulting in a density gradient of 1.077-1.100. After that, the liquid material obtained in the degradation step was flowed into the circuit, and the eluted liquid was sequentially fractionated from the collection port into polystyrene T-type 25 $cm^2$ flasks in increments of about 20 ml and observed with a microscope. Then, it was decided that a large amount of pancreatic islet was contained in the fraction that was obtained after the liquid of about 200 ml had been eluted after the start of the centrifugation, and so about 100 ml of the eluate after that was collected. The collected eluate was put in a 250 ml centrifugal tube, which was then subjected to centrifugation at 224 g to remove the specific gravity liquid. After that, the pancreatic islet was suspended in a CMRL medium again.

Experimental Example 1

Experiment of Preserving Pancreatic Islet

The pancreatic islet dispersion liquid prepared in Reference Example 1 was stored in containers in Example 1 and Comparative Example 1 in increments of 200 ml, through the syringe-connecting port provided to the containers by using a syringe. The thickness of the container on this occasion was about 7 mm. Next, they were preserved under a 5% $CO_2$ atmosphere at 37° C. for about 2 days.

For the survival rate and function of β-cells after the preservation relative to those before the preservation being set to 100%, the pancreatic islet survival rate measurement and in vitro carbohydrate tolerance test of pancreatic islet function were carried out. Specifically, 60 pancreatic islets having a diameter of 150 μm were selected at random, which were distributed into three tubes including 1.67 mM of low concentration glucose. After the incubation at 37° C. for 30 minutes, the supernatant was collected. Next, it was incubated with 16.7 mM of high concentration glucose for 30 minutes and the supernatant was collected in the same way. The insulin concentrations of respective supernatants were measured with ELISA (by Mercodia Inc.) to calculate the survival rate and pancreatic islet function. The pancreatic islet function is a value that is obtained by dividing the insulin amount discharged at the time of the high concentration glucose solution by the insulin amount discharged at the time of the low concentration glucose solution, and is referred to as Stimulation Index (S.I.). The results are shown in Table 1.

TABLE 1

|  | Example 1 | Comparative Ex. 1 |
|---|---|---|
| Survival rate (pancreatic islet residual rate) | 31.9 ± 9.4 (p = 0.38) | 20.9 ± 7.6 |
| Pancreatic islet function (S.I.) | 1.97 ± 0.22 (p = 0.005) | 1.05 ± 0.19 |

As is clear from the results in Table 1, the Example showed a higher survival rate and pancreatic islet function compared with Comparative Example. Thus, the method of the present invention showed high availability in the preservation of the pancreatic islet.

INDUSTRIAL APPLICABILITY

As described above, when preserving the pancreatic islet by using the method, container and kit of the present invention, it is possible to more suitably preserve the pancreatic islet. Thus, since enough time is generated from the preparation of the pancreatic islet to the transplant operation, no burden is imposed on an operator and patient. Furthermore, since the risk of deactivation or death of β-cells due to unsuitable preserving conditions is drastically reduced, the will of a donor is respected.

What is claimed is:

1. A method for preserving pancreatic islet, comprising a step of preserving a liquid containing pancreatic islet separated and purified from a living body in a container, the container comprising
a wall face in contact with the liquid, wherein 100% of the total area of the wall face consists of a film having an oxygen permeation coefficient of 3000 $cm^3/m^2 \cdot day \cdot atm$ or greater and a polymeric material that is low density polyethylene or a polymer blend of low density polyethylene and medium density polyethylene, wherein the film has a pure water contact angle of 85 degrees or greater,
a bag-like figure produced of two of the films, and
a volume of the liquid such that the maximum value of the container thickness, the distance between the two films, is within the range of 3 to 10 mm, when the liquid containing pancreatic islet is stored in the container and the container is placed on a horizontal plane so that the film surface of the container contacts the plane,
wherein the pancreatic islet is suspended in the liquid so that adhesion of the pancreatic islet to the wall face is prevented,
wherein the pancreatic islet has a β-cell activity represented by a survival rate of at least 25% after 1-4 days preservation in the liquid,
wherein the method for preserving pancreatic islet is utilized for a pancreatic islet transplantation comprising 10 to 18 hours after isolating the pancreas to obtaining the pancreatic islet and 1 to 4 days during preservation of the pancreatic islet to the completion of transplant operation of the pancreatic islet.

2. The method for preserving pancreatic islet according to claim 1, wherein at least a part of the wall face of the container consists of a film having a carbon dioxide permeation coefficient of 1000 to 20000 $cm^3/m^2 \cdot da \cdot atm$.

3. The method for preserving pancreatic islet according to claim 2, wherein the container further includes a filter for exchanging a preservative liquid.

4. The method for preserving pancreatic islet according to claim 2, wherein the container has a bag-like figure produced of two of the films, is further provided with a port for injecting and ejecting the liquid, and has a sealed edge portion tapered toward the port.

5. The method for preserving pancreatic islet according to claim 1, wherein the container further includes a filter for exchanging a preservative liquid.

6. The method for preserving pancreatic islet according to claim 1, wherein the container has a bag-like figure produced of two of the films, is further provided with a port for injecting and ejecting the liquid, and has a sealed edge portion tapered toward the port.

7. The method for preserving pancreatic islet according to claim 1, wherein the pancreatic islet that is separated and purified from a living body is obtained prior to the step of preserving using Edmonton Protocol.

* * * * *